(12) United States Patent (10) Patent No.: US 9,238,122 B2
Malhi et al. (45) Date of Patent: Jan. 19, 2016

(54) THROMBECTOMY CATHETER SYSTEMS

(71) Applicant: Covidien LP, Mansfield, MA (US)

(72) Inventors: Arnaz Malhi, Watertown, MA (US); Daniel Hutton, Brighton, MA (US); Manish Deshpande, Canton, MA (US); Philip Shaltis, Sharon, MA (US)

(73) Assignee: Covidien LP, Mansfield, MA (US)

( * ) Notice: Subject to any disclaimer, the term of this patent is extended or adjusted under 35 U.S.C. 154(b) by 124 days.

(21) Appl. No.: 13/630,323

(22) Filed: Sep. 28, 2012

(65) Prior Publication Data

US 2013/0267891 A1 Oct. 10, 2013

Related U.S. Application Data

(60) Provisional application No. 61/591,165, filed on Jan. 26, 2012.

(51) Int. Cl.
*A61M 25/00* (2006.01)
*A61B 17/3203* (2006.01)

(52) U.S. Cl.
CPC ...... *A61M 25/0082* (2013.01); *A61B 17/32037* (2013.01); *A61M 25/0067* (2013.01); *A61M 25/0069* (2013.01)

(58) Field of Classification Search
CPC ............ A61M 25/00; A61M 25/0082; A61M 2025/000067; A61M 2025/0068; A61M 25/0069; A61M 1/00; A61B 17/3203; A61B 17/32037
USPC ............. 604/19, 27, 30, 39, 43; 606/159, 167
See application file for complete search history.

(56) References Cited

U.S. PATENT DOCUMENTS

| 4,487,600 A | * | 12/1984 | Brownlie et al. ............... 604/35 |
| 4,694,828 A | * | 9/1987 | Eichenbaum ..................... 606/6 |
| 4,937,985 A | | 7/1990 | Boers et al. |
| 5,018,670 A | | 5/1991 | Chalmers |
| 5,037,431 A | * | 8/1991 | Summers et al. ............. 606/131 |
| 5,037,432 A | * | 8/1991 | Molinari ........................ 606/131 |
| 5,052,624 A | * | 10/1991 | Boers et al. ................... 239/525 |
| 5,300,022 A | * | 4/1994 | Klapper et al. .................. 604/35 |
| 5,318,518 A | * | 6/1994 | Plechinger et al. ............. 604/43 |

(Continued)

FOREIGN PATENT DOCUMENTS

| CN | 2049956 U | 12/1989 |
| CN | 101394877 A | 3/2009 |

(Continued)

OTHER PUBLICATIONS

Japanese Office Action dated Jan. 21, 2014 on related Japanese Application No. 2013-11957.

(Continued)

*Primary Examiner* — Quynh-Nhu H Vu

(57) ABSTRACT

A thrombectomy catheter system is disclosed which includes a catheter having an exhaust lumen, an infusion lumen and a high pressure tube. The high pressure tube includes a nozzle orifice for forming a high pressure jet of fluid for cutting occlusive material from within a body lumen. The nozzle orifice is positioned to direct the high pressure jet of fluid into the distal end of the exhaust lumen which creates a suctioning effect. The infusion lumen replaces fluid that is removed from the body lumen through the exhaust lumen by a suctioning effect created by the fluid jet.

24 Claims, 11 Drawing Sheets

(56) References Cited

U.S. PATENT DOCUMENTS

| | | | |
|---|---|---|---|
| 5,370,609 A | 12/1994 | Drasler et al. | |
| 5,395,315 A * | 3/1995 | Griep | 604/35 |
| 5,496,267 A * | 3/1996 | Drasler et al. | 604/22 |
| 5,785,675 A | 7/1998 | Drasler et al. | |
| 5,855,549 A * | 1/1999 | Newman | 600/135 |
| 5,871,462 A | 2/1999 | Yoder et al. | |
| 5,989,210 A | 11/1999 | Morris et al. | |
| 5,989,271 A * | 11/1999 | Bonnette et al. | 606/159 |
| 6,096,001 A | 8/2000 | Drasler et al. | |
| 6,129,697 A | 10/2000 | Drasler et al. | |
| 6,135,977 A | 10/2000 | Drasler et al. | |
| 6,193,589 B1 * | 2/2001 | Khalaj | 451/102 |
| 6,216,573 B1 | 4/2001 | Moutafis et al. | |
| 6,224,570 B1 | 5/2001 | Le et al. | |
| 6,258,061 B1 | 7/2001 | Drasler et al. | |
| 6,375,635 B1 | 4/2002 | Moutafis et al. | |
| 6,451,017 B1 | 9/2002 | Moutafis et al. | |
| 6,471,683 B2 | 10/2002 | Drasler et al. | |
| 6,511,493 B1 | 1/2003 | Moutafis et al. | |
| 6,544,209 B1 | 4/2003 | Drasler et al. | |
| 6,558,366 B1 | 5/2003 | Drasler et al. | |
| 6,669,710 B2 | 12/2003 | Moutafis et al. | |
| 6,676,627 B1 | 1/2004 | Bonnette et al. | |
| 6,676,637 B1 * | 1/2004 | Bonnette et al. | 604/165.02 |
| 6,712,757 B2 * | 3/2004 | Becker et al. | 600/121 |
| 6,719,718 B2 | 4/2004 | Bonnette et al. | |
| 6,755,803 B1 | 6/2004 | Le et al. | |
| 6,764,483 B1 | 7/2004 | Bonnette et al. | |
| 6,805,684 B2 | 10/2004 | Bonnette et al. | |
| 6,875,193 B1 | 4/2005 | Bonnette et al. | |
| 6,899,712 B2 | 5/2005 | Moutafis et al. | |
| 6,923,792 B2 | 8/2005 | Staid et al. | |
| 6,926,726 B2 | 8/2005 | Drasler et al. | |
| 6,932,828 B2 | 8/2005 | Bonnette et al. | |
| 6,942,678 B2 | 9/2005 | Bonnette et al. | |
| 6,945,951 B1 | 9/2005 | Bonnette et al. | |
| 6,960,182 B2 | 11/2005 | Moutafis et al. | |
| 6,984,239 B1 | 1/2006 | Drasler et al. | |
| 7,033,317 B2 | 4/2006 | Pruitt | |
| 7,122,017 B2 | 10/2006 | Moutafis et al. | |
| 7,169,161 B2 | 1/2007 | Bonnette et al. | |
| 7,220,243 B2 | 5/2007 | Bonnette et al. | |
| 7,220,269 B1 | 5/2007 | Ansel et al. | |
| 7,226,433 B2 | 6/2007 | Bonnette et al. | |
| 7,337,538 B2 | 3/2008 | Moutafis et al. | |
| 7,431,711 B2 | 10/2008 | Moutafis et al. | |
| 7,717,685 B2 | 5/2010 | Moutafis et al. | |
| 2004/0049149 A1 * | 3/2004 | Drasler et al. | 604/43 |
| 2004/0230211 A1 | 11/2004 | Moutafis et al. | |
| 2005/0159765 A1 | 7/2005 | Moutafis et al. | |
| 2005/0283150 A1 | 12/2005 | Moutafis et al. | |
| 2006/0229550 A1 | 10/2006 | Staid et al. | |
| 2006/0264808 A1 | 11/2006 | Staid et al. | |
| 2008/0195058 A1 | 8/2008 | Moutafis et al. | |
| 2009/0076440 A1 | 3/2009 | Moutafis et al. | |
| 2009/0192498 A1 | 7/2009 | Andrew et al. | |
| 2009/0306692 A1 | 12/2009 | Barrington et al. | |
| 2010/0010524 A1 | 1/2010 | Barrington et al. | |
| 2010/0228273 A1 | 9/2010 | Staid et al. | |
| 2011/0015564 A1 * | 1/2011 | Bonnette et al. | 604/22 |
| 2011/0091331 A1 | 4/2011 | Moutafis et al. | |

FOREIGN PATENT DOCUMENTS

| | | |
|---|---|---|
| CN | 101460101 A | 6/2009 |
| CN | 101730507 A | 6/2010 |
| CN | 102319097 A | 8/2012 |
| EP | 0 485 133 | 5/1992 |
| JP | 06-205785 | 7/1994 |
| JP | 2000-140121 | 5/2000 |
| JP | 2001-161700 | 6/2001 |
| WO | 9005493 A1 | 5/1990 |
| WO | 06-197951 | 7/1994 |
| WO | 0176518 A1 | 10/2001 |

OTHER PUBLICATIONS

European Search Report dated Apr. 16, 2013 in copending European Application No. 13 15 0889.

First Office Action, and translation thereof, from Counterpart Chinese Patent Application No. 201310028600.4, dated Sep. 23, 2014, 15 pp.

* cited by examiner

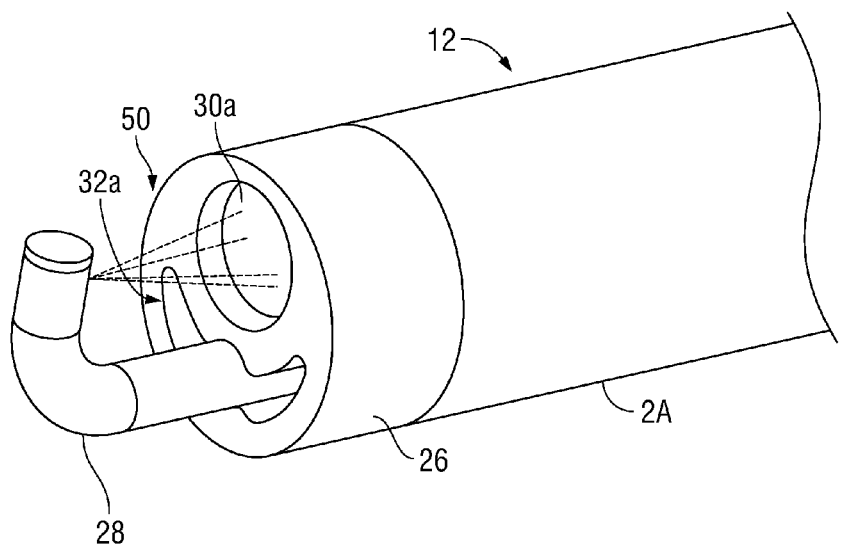
FIG. 2
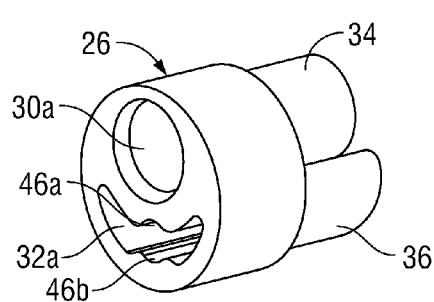 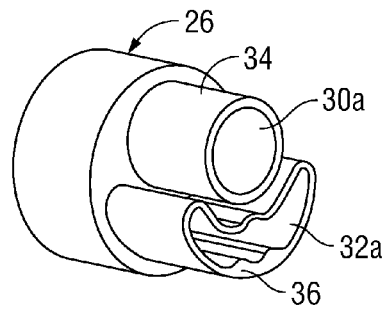
FIG. 3A  FIG. 3B

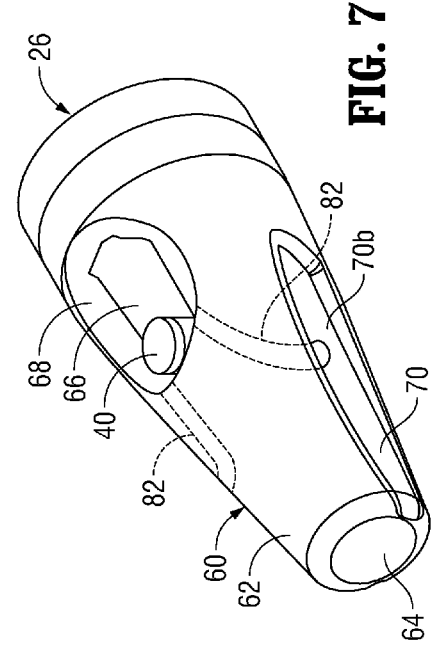
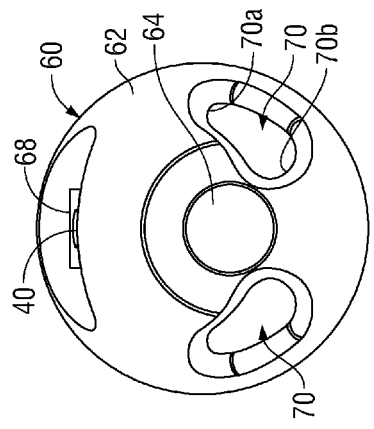
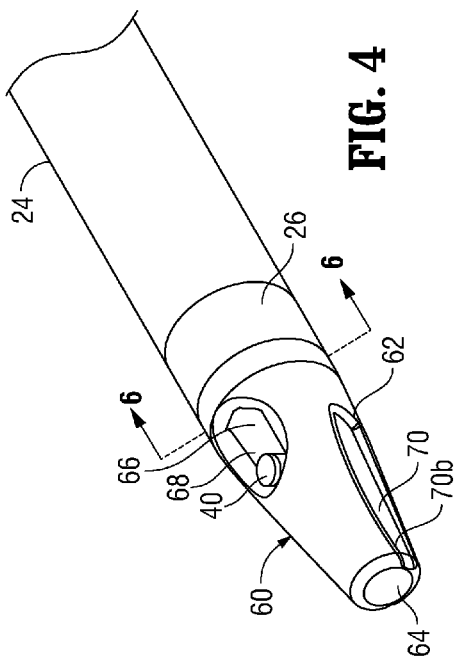
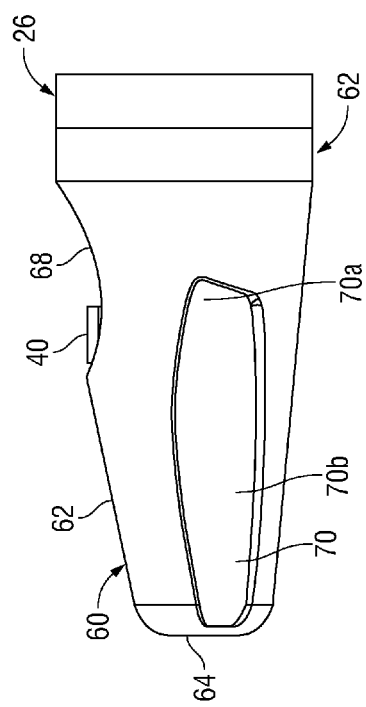

THROMBECTOMY CATHETER SYSTEMS

CROSS REFERENCE TO RELATED APPLICATIONS

This application claims the benefit of and priority to U.S. Provisional Application Ser. No. 61/591,165, filed Jan. 26, 2012, the entire contents of which is incorporated herein by reference.

TECHNICAL FIELD

The present disclosure relates to systems for removing occlusive materials from within blood vessels, and more particularly, to thrombectomy catheter systems.

BACKGROUND

Apparatus for removing occlusive material from a body lumen to maintain the patency of the body lumen are well known in the art. These apparatus may be of the mechanical, electrical or chemical type. Typically, each type of apparatus is particularly suited for removal of a particular type of occlusive material from the body lumen such as chronic clots, sub-acute clots or acute clots. For example, apparatus which infuse chemicals into a body lumen to remove occlusive material from the lumen are more effective in removing acute clots and are less effective in removing chronic clots.

One difficulty associated with designing an apparatus for removing all types of occlusive material from a body lumen is creating a device that can effectively remove occlusive material while at the same time minimizing the likelihood of causing damage to the body lumen.

Accordingly, it would be desirable to provide an apparatus capable of effectively removing a variety of different occlusive materials from a body lumen while minimizing the risk of causing damage to the body lumen.

SUMMARY

The present disclosure is directed to a thrombectomy catheter system which includes a thrombectomy catheter including a catheter body defining an exhaust lumen and an infusion lumen and including a high pressure tube. In one aspect, the high pressure tube has a nozzle orifice positioned to direct a fluid jet into a distal opening of the exhaust lumen. A source of infusion fluid communicates with a proximal end of the infusion lumen and a fluid control device is fluidly coupled between the thrombectomy catheter and the source of infusion fluid. The fluid control device is adapted to regulate a flow rate of infusion fluid from the source of infusion fluid to the infusion lumen of the thrombectomy catheter.

In one embodiment of the thrombectomy catheter system, the infusion fluid and fluid in the high pressure tube is saline.

In another embodiment, the thrombectomy catheter system includes a high pressure tube which defines a bent portion at the distal end of the high pressure tube. The nozzle orifice is positioned in the bent portion which extends along an axis which is substantially transverse to a longitudinally axis of the thrombectomy catheter.

In another embodiment, the thrombectomy catheter system includes a source of high pressure fluid communicating with the high pressure tube. The source of high pressure fluid supplies high pressure fluid to the high pressure tube at a pressure of between about 100 psi and about 10,000 psi.

In another embodiment, the thrombectomy catheter system includes a substantially rigid positioning band secured to a distal end of the catheter body. The positioning band defines an exhaust lumen which communicates with the exhaust lumen of the catheter body and an infusion lumen which communicates with the infusion lumen of the catheter body.

In one embodiment, the high pressure tube is bonded to the positioning band. The high pressure tube and the positioning band may be formed of either metal or plastic.

In one embodiment, the high pressure tube extends through the infusion lumen of the positioning band and the catheter body.

In one embodiment, the infusion lumen of the positioning band defines a pair of concavities dimensioned to receive the high pressure tube and prevent lateral movement of the high pressure tube in relation to the positioning band.

In one embodiment, the infusion lumen in the positioning band is adjacent to the exhaust lumen of the positioning band, and covers an arc angle of at least 140°.

In another embodiment, a fluid control device is provided which includes an adjustable valve adapted to regulate the fluid flow rate into the infusion lumen of the thrombectomy catheter from the source of infusion fluid.

In one embodiment, the fluid control device includes a fluid pump for supplying infusion fluid to the thrombectomy catheter from the source of infusion fluid. The fluid pump or the adjustable valve may be adapted to vary the flow rate of infusion fluid to the thrombectomy catheter cyclically.

In another embodiment, the thrombectomy catheter includes an atraumatic tip which includes a pair of infusion channels which communicate with the infusion lumen of the positioning band and a reservoir for receiving the bent portion of the high pressure tube. The reservoir has an upper opening defining a cutting window.

In another embodiment, the infusion channels extend distally of the bent portion of the high pressure tube and enable the longitudinal or transverse infusion of infusion fluid at the tip.

In another embodiment, the atraumatic tip has microchannels to enable fluidic coupling between the central cavity and the infusion channels. The microchannels are either orifices in the wall separating the central cavity and the infusion channels or are open channels formed by depressions on the surface of the atraumatic tip.

In another embodiment, the thrombectomy catheter system includes a guide catheter defining a guide lumen dimensioned to receive the thrombectomy catheter, a proximal balloon, and a distal balloon.

In another embodiment, a portion of the guide catheter between the proximal balloon and the distal balloon has a sinusoidal shape and defines a plurality of openings which enable the aspiration of occlusive material into the thrombectomy catheter.

In yet another embodiment, the thrombectomy catheter system may include a portion of the guide catheter between the proximal balloon and the distal balloon that is flexible and defines a plurality of openings which enable the aspiration of occlusive material from the vessel into contact with the thrombectomy catheter. The flexibility of the portion of the guide catheter is such that a sinusoidal shape imparted to the thrombectomy catheter is taken by the guide catheter once the thrombectomy catheter is inserted into the guide catheter such that the guide catheter is then sinusoidal in shape.

In one embodiment, a sensor is positioned to measure the pressure within a body lumen. The sensor may be connected to the fluid control device to control operation of the fluid control device.

In one embodiment, a recirculation channel is positioned to recirculate fluid from within the exhaust lumen back into a body lumen. A filter may be positioned upstream of the recirculation channel which is sized to prevent passage of solid particles into the recirculation channel.

In one embodiment, the exhaust lumen is divided into a first exhaust lumen and a second exhaust lumen by a dividing wall and the filter and recirculation channel are positioned in the first exhaust lumen. The filter may be positioned at one end of the first exhaust lumen and angled to direct solid particles into the second exhaust lumen.

In one embodiment, a recirculation channel is provided which extends between the exhaust lumen and the high pressure tube. A filter may be provided in the recirculation channel which enables small solid particles to enter the high pressure tube to create a sand blasting effect adjacent the nozzle orifice.

In one embodiment, structure configured to break up occlusive material is positioned within the exhaust lumen. The structure may include a grate having sharp cutting edges. Alternately, the structure may include a rotatable turbine configured to grind occlusive material.

In one embodiment, the thrombectomy catheter includes a body defining a window between the nozzle orifice and an inlet to the exhaust lumen, and a cage is positioned adjacent the window to cover the window.

The device described herein can be implemented to realize one or more of the following advantages. The thrombectomy catheter employs a high pressure waterjet for removing occlusive materials from within blood vessels, which may be safer than mechanical cutting devices. The presently disclosed thrombectomy catheter systems are particularly suited for treatment and removal of various clots, such as deep venous thrombosis (DVT), no matter the age or organization of the thrombosis or clot. For example, the thrombectomy catheter may remove both acute and chronic clot. The disclosed thrombectomy catheter may be configured in various ways to protect the body lumen while enabling the waterjet to remove the clot. The body lumen may be protected by specific structure positioned adjacent the waterjet that provides a physical barrier against cutting the body lumen. Further, the body lumen may be protected by monitoring the pressure in the body lumen adjacent to the waterjet to signal a controller to stop cutting (i.e., turn the waterjet off) or to infuse fluid into the body lumen.

Also, the disclosed thrombectomy catheter provides an infusion liquid to provide fluid balance within the body lumen to prevent the body lumen from being excessively drained of blood and fluid.

Further, a separate means for transporting the clot out of the body lumen through the thrombectomy catheter is not required since the high pressure fluid provides the necessary motive force to move the clot through the thrombectomy catheter. Further still, the disclosed thrombectomy catheter may be provided with a means to macerate the removed clot to better transfer the clot through the thrombectomy catheter. The means to macerate the clot may return some of the smaller particles of the macerated clot back into the fluid stream to help further break up the clot.

Other features and advantages of the disclosure are apparent from the following description, and from the claims.

BRIEF DESCRIPTION OF THE DRAWINGS

Various embodiments of the presently disclosed thrombectomy catheter system are described herein with reference to the drawings, wherein:

FIG. 2 is a side, perspective view of the distal portion of one embodiment of the presently disclosed thrombectomy catheter of the system shown in FIG. 1;

FIG. 3A is a front perspective view of a positioning band of the thrombectomy catheter shown in FIG. 2;

FIG. 3B is a rear perspective view of the positioning band shown in FIG. 3A;

FIG. 4 is a side perspective view of the distal portion of an alternative embodiment of the presently disclosed thrombectomy catheter;

FIG. 7 is a perspective view of the distal end of the catheter body and catheter tip of the thrombectomy catheter shown in FIG. 4;

FIG. 8 is a side view of the catheter body and catheter tip shown in FIG. 4;

FIG. 9 is a front view of the thrombectomy catheter shown in FIG. 4;

DETAILED DESCRIPTION OF EMBODIMENTS

Figure 1:
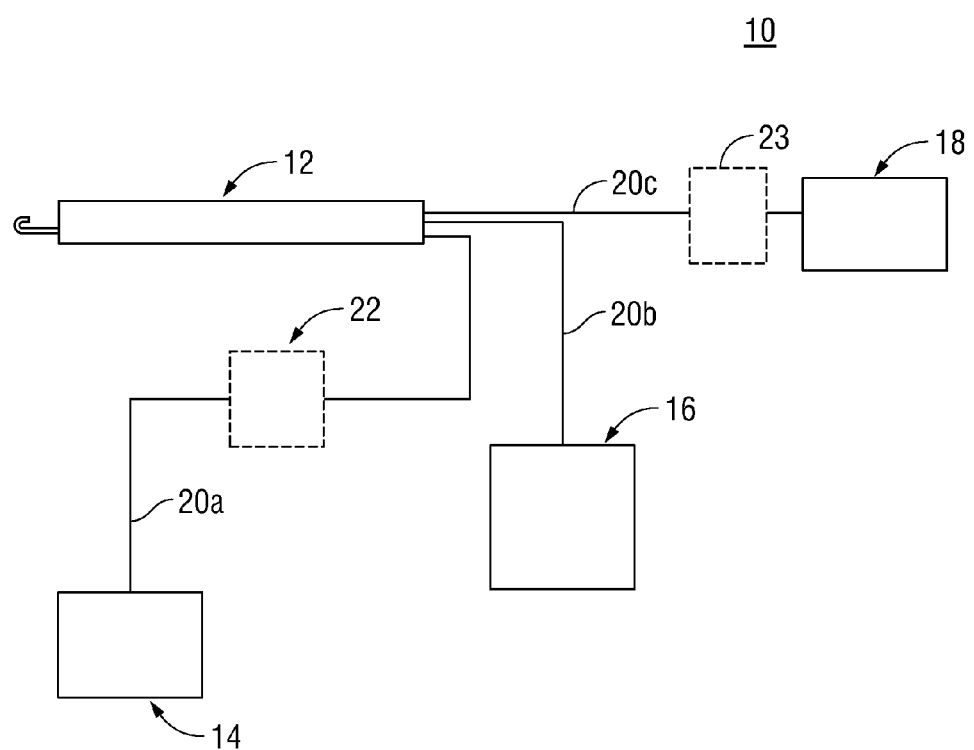
FIG. 1 is a schematic view of one embodiment of the presently disclosed thrombectomy catheter system.

Embodiments of the presently disclosed thrombectomy catheter system will now be described in detail with reference to the drawings wherein like reference numerals identify similar or identical elements in each of the several views. As used herein, the term "distal" refers to that portion of the presently disclosed thrombectomy catheter system, or component thereof, that is furthest from the user, such as a physician, during proper use, while the term "proximal" refers to that portion of the thrombectomy catheter system, or component thereof, that is closest to the user during proper use. Additionally, the term "lumen" should be understood to include any lumen within the body, either natural or artificial, such as, for example, blood vessels, blood vessel grafts, fistulas, and the like. Moreover, the term "occlusion" should be understood to encompass any partial or total blockage of a lumen, such as, for example, thrombus, atheromas, plaque, tumors and the like.

FIG. 1 is a schematic view of one embodiment of the presently disclosed thrombectomy catheter system which is shown generally as 10. Thrombectomy catheter system 10 includes a thrombectomy catheter 12, a source of infusion fluid 14, a source of high pressure fluid 16, and a reservoir 18 for receiving fluid exhausted from the surgical site. Each of the sources of infusion fluid 14 and high pressure fluid 16, and the exhaust fluid reservoir 18, communicate with the thrombectomy catheter 12 via a suitable fluid conduit 20a-20c, respectively. A control device 22 may be provided in the fluid conduit 20a connecting the infusion fluid source 14 to the thrombectomy catheter 12. The control device 22 may include a pump or valve which is operable to regulate the flow rate of infusion fluid to the thrombectomy catheter 12, as will be discussed in further detail below.

Figure 2A:
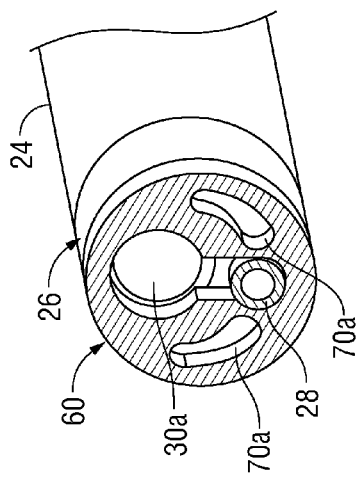
FIG. 2A is a perspective view of the distal end of the catheter body shown in FIG. 2 with the distal end of the high pressure tube cutaway.
Figure 6:
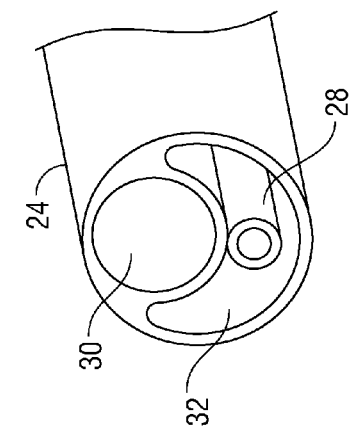
FIG. 6 is a perspective, cross-sectional view taken along section lines 6-6 of FIG. 4.

Referring to FIGS. 2-3B, thrombectomy catheter 12 includes a catheter body 24, a positioning band 26 and a high pressure tube 28. Catheter body 24 of catheter 12 defines at least two lumens and may be formed, such as by extrusion, from any suitable biocompatible material sufficiently pliable to facilitate insertion of the catheter 12 into a body lumen. Suitable materials include, but are not limited to, polymeric materials, elastomeric materials, for example, silicone and fabric materials, or a synthetic resin, for example, polyurethane, polyethylene, polypropylene, nylons, polytetrafluoroethylene (PTFE), polyether ether ketone (PEEK), PEBAX®, or polyimide. In one embodiment, catheter body 24 defines an exhaust lumen 30 and an infusion lumen 32 (see FIG. 2A). The exhaust lumen 30 defines a lumen to exhaust fluid and includes a proximal end which is in fluid communication with fluid conduit 20c (FIG. 1) and exhaust fluid reservoir 18. The infusion lumen 32 defines a lumen to infuse fluid and is in fluid communication with the fluid conduit 20a (FIG. 1) and the infusion fluid source 14. Although exhaust lumen 30 is illustrated to be circular and infusion lumen 32 is illustrated to be crescent shaped, a variety of other configurations are envisioned for the exhaust and infusion lumens 30 and 32.

Positioning band 26 is supported on the distal end of the catheter body 24 and defines exhaust and infusion lumens 30a and 32a which communicate with exhaust and infusion lumens 30 and 32, respectively, of catheter body 24. Positioning band 26 includes a first proximal extension 34 which has a shape which corresponds to the shape of exhaust lumen 30 of catheter body 24 and a second proximal extension 36 which has a shape that corresponds to the shape of the infusion lumen 32 of the catheter body 24. The proximal extensions 34 and 36 are receivable in the distal ends of exhaust and infusion lumens 30 and 32 of catheter body 24 to frictionally secure the positioning band 26 to the distal end of catheter body 24. Alternatively, or in addition to frictional engagement, the positioning band 26 may be secured to the distal end of catheter body 24 by other fastening techniques including using adhesives, welding, crimping or the like. In one embodiment, the infusion lumen 32a in the positioning band 26 is adjacent to the exhaust lumen 30a of the positioning band 26, and may have an area that extends for an arc angle θ greater than about 140° and preferably greater than 180°. See FIG. 18. The positioning band 26 may be formed from a suitable biocompatible plastic including polymeric materials, including thermoplastics or the like, or a suitable biocompatible metal, including stainless steel, titanium or the like.

Figure 5:
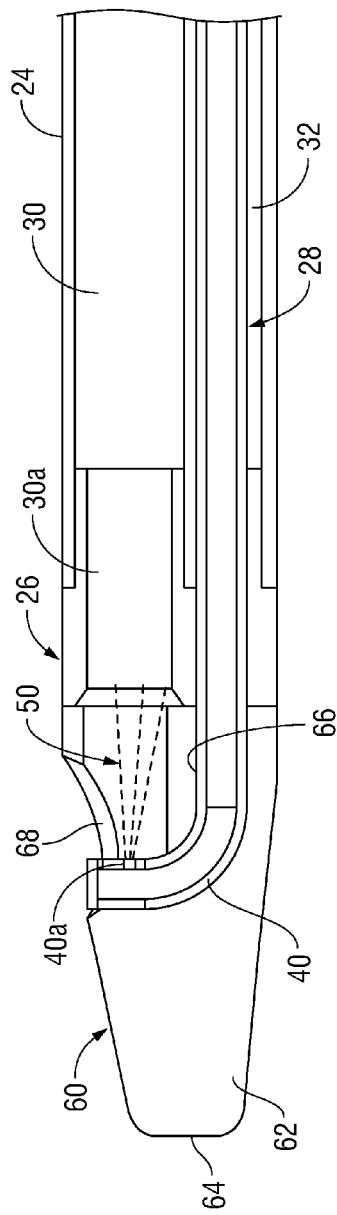
FIG. 5 is a side cross-sectional view of the thrombectomy catheter shown in FIG. 4.

The high pressure tube 28 is positioned to extend through the infusion lumen 32 and includes a closed distal end and a bent portion 40 defining a nozzle orifice 40a (see FIG. 5). As illustrated, the bent portion 40 is positioned transversely to the longitudinal axis of catheter body 24 such that the nozzle orifice 40a is positioned to direct a jet 50 of fluid in a direction substantially parallel to the longitudinal axis of the catheter 12 into the exhaust lumen 30a of the positioning band 26. Although bent portion 40 is shown to be about 90 degrees offset from the longitudinal axis of the catheter body 24, it is envisioned that bent portion 40 may be bent about 180 degrees and the nozzle orifice 40a can be formed in the distal end of the high pressure tube 28. In one embodiment, the high pressure tube 28 is formed from a metal, such as Nitinol or stainless steel. Alternatively, the high pressure tube 28 may be formed from a thermoplastic material such as a polyether ether ketone (PEEK). The high pressure tube 28 may be secured or bonded to the positioning band 26 using, for example, adhesives, welding or the like, to ensure that nozzle orifice 40a of tube 28 is properly positioned in relation to exhaust lumen 30a of positioning band 26 as will be discussed in further detail below. Alternatively, the high pressure tube 28 may be slidably positioned in relation to the exhaust lumen 30a of positioning band 26 to enable the spacing between the nozzle orifice 40a and the exhaust lumen 30a to be selectively varied. In one embodiment, the positioning band 26 includes upper and lower concavities 46a and 46b (FIG. 3A) which are dimensioned to receive the high pressure tube 28 and to minimize lateral movement of tube 28 in relation to band 26.

As discussed above, the nozzle orifice 40a may be spaced distally of exhaust lumen 30a of positioning band 26 a predetermined distance. The nozzle orifice 40a may be cylindrical in shape to produce a substantially symmetrical conical jet (see FIG. 2). In one embodiment, the diameter of nozzle orifice 40a is between about 0.001 to 0.01 inch. Alternatively, the nozzle orifice 40a may be conical with the inlet opening of the nozzle orifice 40a having a larger diameter than the exhaust opening of the nozzle orifice 40a. Such a conical nozzle orifice is better suited for use with lower fluid pressures. As discussed above and shown in FIG. 2, the fluid jet 50 produced by the nozzle orifice 40a is configured to be received entirely within the exhaust lumen 30a of the positioning band 26.

In one embodiment of the presently disclosed thrombectomy catheter 12, the diameter of the exhaust lumen 30a is about 0.050 inch, the diameter of the cylindrical jet nozzle 40a is about 0.005 inch and the spacing between nozzle orifice 40a and exhaust lumen 30a is about 0.008 inch. Alternatively, the spacing between nozzle orifice 40a and exhaust lumen 30a is about 0.060 inches. Alternately, other dimensions may be selected to optimize aspiration of fluid flow through the exhaust lumens 30a and 30 of catheter 12.

Referring to FIGS. 1 and 2, when thrombectomy catheter system 10 is used to remove occlusive materials from within a blood vessel, the thrombectomy catheter 12 is positioned within the venous system of a patient using standard percutaneous access techniques. Although not shown, catheter body 24 and positioning band 26 may be formed to include a guidewire bore to assist in placement of catheter 12 within a vessel lumen of a patient. Alternatively, a guidewire may be passed down the infusion lumen 32 to effect placement of the catheter 12. With the catheter 12 positioned within a vessel lumen, the catheter 12 is advanced to position the distal end of catheter 12 within or in abutment with the occlusive material. Pressurized fluid, such as saline or water, is then supplied at a pressure of from about 100 psi to about 10,000 psi from high pressure fluid source 16 through fluid conduit 20b to the high pressure tube 28. Alternatively, a thrombolytic agent such as tPA may be mixed in with the pressurized fluid. The high pressure fluid travels through high pressure tube 28 and exits nozzle orifice 40a (FIG. 5) as a high pressure fluid jet 50. As the high pressure fluid jet 50 passes into exhaust lumen 30a of positioning band 26, the fluid jet 50 causes entrainment of surrounding fluid and occlusive material into the jet in the proximity of the exhaust lumen 30a. Depending on the various parameters disclosed, a vacuum is created and may be in the range of 10-760 mmHg. When this occurs, occlusive material is drawn into contact with the high pressure fluid jet 50 and is cut. The occlusive material which has been cut, and fluid within the vessel lumen such as blood, is evacuated from the vessel lumen into the exhaust lumen 30a, 30 of the catheter body 24 where it flows proximally from catheter 12 to conduit 20c and into exhaust fluid reservoir 18.

In order to replace the fluid which is removed from the vessel lumen as a result of the suctioning effect created by the high pressure fluid jet 50 within the vessel lumen, fluid is supplied or infused into the vessel lumen from infusion fluid source 14 through infusion lumen 32 of catheter body 24. The infusion lumen 32 may also be used to introduce a thrombolytic agent or contrast medium into a vessel lumen as described below. In one embodiment, the infusion fluid, which may be saline, is passively drawn into the infusion lumen 32 by the negative pressure created in the vessel lumen adjacent the distal end of the infusion lumen 32 by the high pressure jet 50. In such an embodiment, the control device 22 which may be positioned in the fluid conduit 20a connecting the infusion fluid source 14 to the catheter 12, may include an adjustable valve which can be selectively operated to control the infusion fluid flow rate to the catheter 12. In such an embodiment, the flow rate of fluid supplied to the infusion lumen 32 of catheter 12 may be cyclically varied by the adjustable valve to assist in breaking up the occlusive material. Specifically, the pulsation of fluid caused by cyclically varying the flow rate of the fluid supplied through the infusion lumen 32 may help to disrupt or break up the occlusive material. In other passive embodiments, a control device 22 may not be present, and the fluid within the infusion fluid source 14 may be freely moved by the vacuum created within the vessel lumen.

Figure 1A:
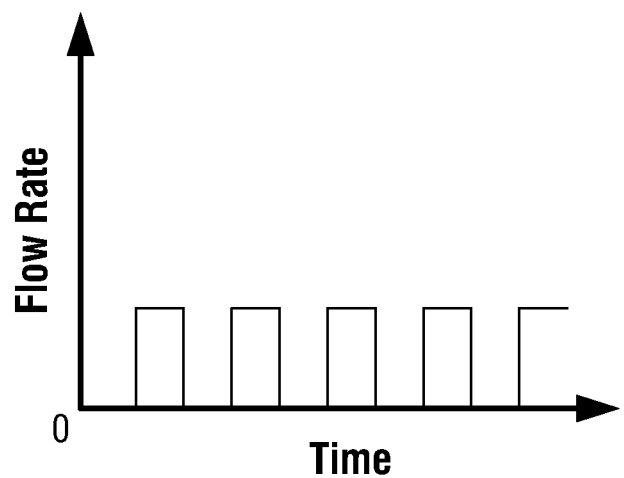
FIG. 1A is a graph illustrating the infusion fluid flow rate per unit of time for one embodiment of the presently disclosed system.
Figure 1B:
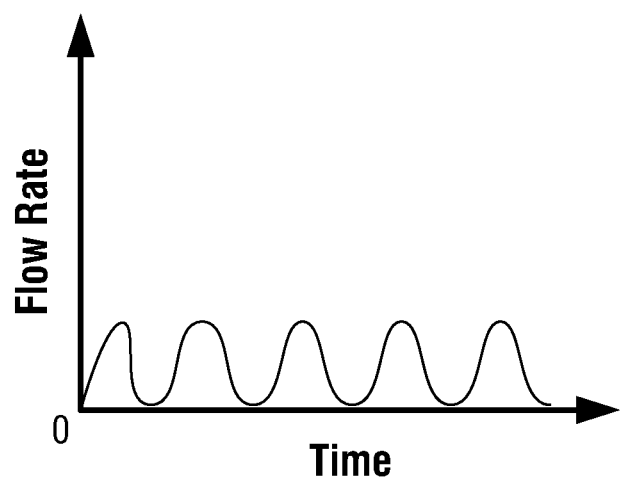
FIG. 1B is a graph illustrating the infusion fluid flow rate per unit of time for another embodiment of the presently disclosed system.

In an alternative embodiment, the control device 22 may include a pump, such as a gear pump or peristaltic pump, to provide a pressurized flow of infusion fluid to the infusion lumen 32 of catheter 12. In such an embodiment, the flow rate of fluid supplied to the infusion lumen 32 of catheter 12 may be cyclically varied to assist in breaking up the occlusive material as discussed above. Cyclically varying the flow rate of the fluid supplied to the infusion lumen 32 of the catheter 12 over time may also minimize the likelihood of a wall of the vessel lumen being drawn into contact with the high pressure jet 50. The cyclical variation of the flow rate may be in the form of a square wave or sinusoidal wave as shown in FIGS. 1A-1B, and may have a frequency in the range of 0.5 to 2.0 Hz.

Referring to FIG. 1, a restrictor 23 may be provided in fluid conduit 20c connecting the exhaust lumen 30 of the catheter 12 to the exhaust fluid reservoir 18. The restrictor 23 may include a mechanical device for compressing or crimping the fluid conduit 20c. Alternatively, other variable restrictor devices may be incorporated into fluid conduit 20c. The restrictor 23 functions to selectively vary the amount of fluid aspirated due to entrainment created by the high pressure fluid jet 50 and thus may enable control of the vacuum created at the distal end of the exhaust lumen 30. In one embodiment, the restrictor 23 may be selectively operated to periodically change the restriction over time. Alternately, a flow meter (not shown) may be provided to measure the fluid flow rate of fluid being aspirated in fluid conduit 20C attached to the reservoir 18 and the restrictor 23 can be operated to control the fluid flow rate in the exhaust lumen 30 to match the fluid flow rate in the infusion lumen 32.

In one embodiment, a pressure sensor is integrated into the thrombectomy catheter to assist in balancing the volume of fluid aspirated from a body lumen with the volume of fluid infused into the body lumen. Referring again to FIG. 2, one or more sensors 80 a-c may be positioned at a variety of locations on the thrombectomy catheter 12, including on the high pressure tube 28 (80c), on the front face of the positioning band 26 (80b), and/or on the outer surface of the positioning band 26 (80a). Alternatively, the sensors may be positioned at other external or internal locations on the thrombectomy catheter 12. In one embodiment, the sensors are low profile fiber optic sensors such as those manufactured by Fiso Technologies, Inc. or Opsens, Inc. Alternately, other types of pressure sensors may be used to measure the pressure within a body lumen being treated by a thrombectomy catheter. The location of the sensor should be selected to provide an accurate measurement of the pressure within the body lumen, not the pressure immediately adjacent the distal end of the catheter 12. As such, the best place for sensor placement may be a location spaced from the distal end of the exhaust lumen 30a, 30, particularly a location that is shielded from the fluid flow into and out of the catheter 12.

Alternatively, a sensor 80 may be positioned within a lumen of the catheter 12 (not shown), or on accessories of the catheter such as on a guidewire or a separate guide catheter. In addition, a separate pressure monitoring lumen (not shown) may be provided in the catheter 12 which communicates with the body lumen and communicates with a strain gauge or the like externally of the body to monitor the pressure of fluid within the body lumen. It is noted that if a sensor is positioned within an existing lumen of the catheter 12 such as in the exhaust lumen 30, flow through the lumen must be stopped prior to taking a pressure measurement to obtain a reading which reflects the pressure within the body lumen and not the pressure within the exhaust lumen. In such an embodiment, the flow restrictor 23 may be used to cyclically stop flow to enable periodic measurements of the pressure within the body lumen.

The purpose of providing a pressure sensor to measure pressure within a body lumen is to maintain balance between the volume of fluid removed from the body lumen through the exhaust lumen 30 and the volume of fluid infused into the body lumen through infusion lumen 32. In use, prior to operating the catheter 12, the lumen pressure is measured to establish a baseline pressure within the lumen. Thereafter, high pressure fluid is supplied through the high pressure tube 28 such that jet 50 passes into exhaust lumen 30a, 30. As the jet 50 passes into the exhaust lumen 30a, 30, a venturi effect is created which draws a vacuum around the exhaust lumen 30a and within the body lumen such that fluid including occlusive material is drawn into the exhaust lumen 30, 30a. When the pressure sensor 80 senses that the pressure within the body lumen has dropped below a threshold pressure, for example, 90% of the lumen baseline pressure, a signal is provided to begin infusion through infusion lumen 32. When a second threshold pressure is reached, for example, 105% of the baseline pressure, a signal is provided to stop infusion. The process of starting and stopping infusion can be automatically controlled using known fluid control devices. Alternatively, the sensors may be used to operate the control device 22 or the restrictor 23 to balance fluid flow to and from the catheter 12.

Although the thrombectomy catheter 12 described above is best suited for removal of acute to sub-acute occlusive material, catheter 12 is fully capable of removing all types of occlusive material from within a vessel lumen, including chronic clots. To remove all types of occlusive material from a vessel lumen, the distal end of the catheter 12 must be pushed into the occlusive material to enable the occlusive material to be positioned adjacent the distal end of catheter 12 such that the occlusive material can be drawn into the jet 50, cut, and macerated.

Referring to FIGS. 4-8, in order to minimize the likelihood that a vessel lumen may be damaged during insertion or manipulation of catheter 12 into or within a vessel lumen, catheter 12 may be fitted with an atraumatic tip 60. Atraumatic tip 60 includes a body 62 having a height and width which decrease from the proximal end of body 62 towards the distal end of the body 62 such that the distal end defines a blunt surface 64. Alternatively, the distal end of the body 62 may be more pointed to further enable the catheter 12 to enter the occlusive material. The body 62 also defines a central cavity 66, an upper opening or cutting window 68 for receiving occlusive material, and a pair of infusion channels 70 which communicate with the infusion lumen 32a of the positioning band 26 and the infusion lumen 32 of catheter body 24. The infusion channels 70 may include an enclosed portion 70a and an open portion 70b. Infusion channels 70 each may have a proximal end of the open portion 70b generally longitudinally aligned with the nozzle orifice 40a and a distal end extending distally of nozzle orifice 40a. The distal opening of the infusion channels 70 in the atraumatic tip 60 may be longitudinal (as shown in FIGS. 7-9) or transverse (not shown).

The atraumatic tip 60 is secured to the distal end of catheter body 24 using any known fastening technique including adhesives, welding or the like. When tip 60 is secured to the catheter body 24, the bent portion 40 of high pressure tube 28 is positioned within central cavity 66 of atraumatic tip 60 such that nozzle orifice 40a is aligned with exhaust lumen 30a of positioning band 26.

The atraumatic tip 60 provides several advantages to the presently disclosed thrombectomy catheter 12. More specifically, the tapered configuration of atraumatic tip 60 may assist in positioning the distal end of catheter 12 within the occlusive material to facilitate positioning of the occlusive material within the high pressure jet 50. In addition, the configuration and positioning of infusion channels 70 along sidewalls of atraumatic tip 60 at a longitudinal position adjacent to or distally of nozzle orifice 40a may create a recirculation pattern of fluid within the vessel lumen adjacent the atraumatic tip 60 of the catheter which will assist in entry of the catheter 12 into tough occlusive material and removal of the occlusive material from the vessel lumen. Further still, the tapered configuration of the atraumatic tip 60 may further enable the occlusive material to enter into the cutting window 68. Specifically, as the atraumatic tip 60 pushes into the occlusive material, and the occlusive material moves along the inclined plane of the atraumatic tip 60, any resiliency in the occlusive material will push back against the atraumatic tip 60, and thus into the cutting window 68.

In an alternative embodiment shown in phantom in FIG. 7, one or more microchannels 82 may be provided in body 62 of tip 60 between infusion channels 70 and cavity 66. Microchannels 82 maintain a path for infusion fluid to flow between infusion lumen 32 of catheter body 24 and central cavity 66 of atraumatic tip 60. In a situation where the atraumatic tip 60 is positioned within the occlusive material such that channels 70 are obstructed, the microchannels 82 enable fluid to circulate within the atraumatic tip 60 between the infusion lumen 32, 32a and the central cavity 66. Alternatively, the microchannels 82 may be formed along an outer surface of the atraumatic tip 60, and extend between the infusion channels 70 and the cutting window 68.

In another embodiment, the atraumatic tip 60 has microchannels 82 to enable fluidic coupling between central cavity 66 and the infusion channels 70. The microchannels 82 are either orifices in the wall separating the central cavity 66 and the infusion channels 70 or are open channels formed by depressions on the surface of the atraumatic tip 60 between the infusion channels 70 and the cutting window 68.

Figure 10:
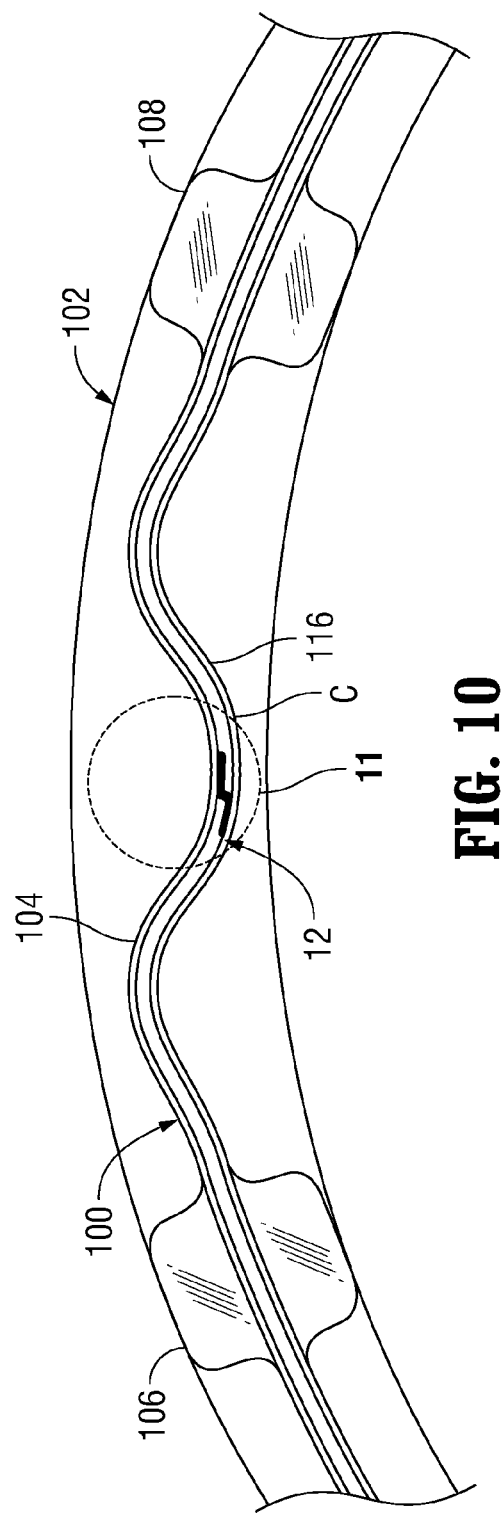
FIG. 10 is a side schematic view of an alternate embodiment of the presently disclosed thrombectomy catheter system including a thrombectomy catheter and a guide catheter.
Figure 11:
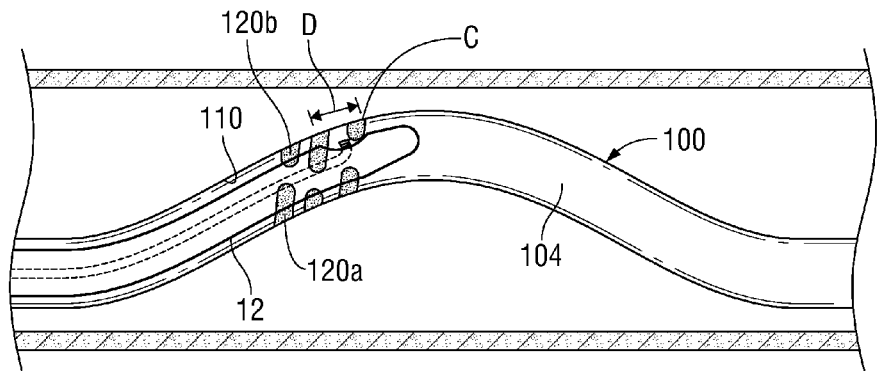
FIG. 11 is an enlarged view of the indicated areas of detail shown in FIG. 10.
Figure 12:
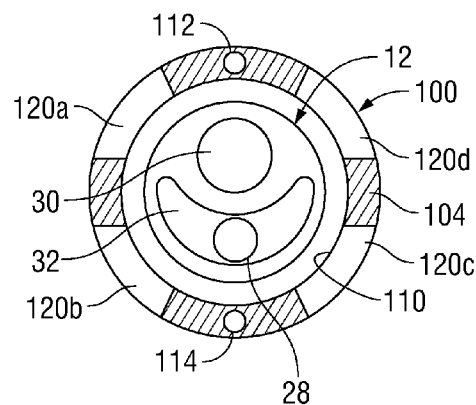
FIG. 12 is a cross-sectional view taken along section lines 12-12 of FIG. 11.

Referring to FIGS. 10-12, a guide catheter 100 may be used to assist in positioning thrombectomy catheter 12 within a vessel lumen 102 (FIG. 10). In one embodiment, the guide catheter 100 includes a guide catheter body 104, a proximal balloon 106 and a distal balloon 108. The guide catheter body 104 may be formed from nylons, polyurethanes, or elastomers such as Pebax®, and may include a reinforcing materials such as stainless steel or Nitinol. The guide catheter body 104 defines a plurality of lumens including a guide lumen 110 dimensioned to receive the thrombectomy catheter 12, an inflation lumen 112 for inflating/deflating the proximal balloon 106 and an inflation lumen 114 for inflating/deflating the distal balloon 108. The guide catheter 100 may be an appropriate size, such as, for example, a 10 F or 12 F catheter. Alternatively, a single inflation lumen may be provided for both the proximal and distal balloons 106 and 108. The guide catheter 100 may also define an additional lumen (not shown) for infusion of saline or a thrombolytic agent, such as a tissue plasminogen activator (tPA), streptokinase, urokinase, or heparin, into the vessel lumen.

Referring to FIG. 10, at least a portion of the guide catheter 100 between the proximal and distal balloons 106 and 108 includes a sinusoidal shape 116. As shown, the sinusoidal shape 116 may extend the entire length of the guide catheter 100 between the proximal and distal balloons 106 and 108. In addition, the sinusoidal shape 116 may be formed by heat setting a PEEK material. Alternately, other methods of forming the sinusoidal shape 116 are envisioned. Alternately, a sinusoidal shape may be imparted to the thrombectomy catheter 12. In such a case, at least a portion of the guide catheter 100 between the proximal and distal balloons 106 and 108 will be flexible enough to take the sinusoidal shape when the thrombectomy catheter 12 is inserted into the guide catheter 100.

As shown in FIG. 12, the guide catheter 100 includes a series of openings 120a-120d positioned about the catheter to provide access to a vessel lumen from within the guide catheter 100.

In use, the guide catheter 100 may be positioned within a vessel lumen using standard placement techniques (such as using a guidewire) such that the occlusive material is positioned between the proximal balloon 106 and the distal balloon 108. The balloons 106 and 108 can be inflated to confine the occlusive material between the balloons within the vessel lumen. Thereafter, if desired, a thrombolytic agent such as tPA can be infused into the vessel lumen through the additional lumen (not shown) provided in the guide catheter to treat the occlusive material chemically. Although the thrombolytic agent could be delivered into the vessel lumen through different passages of the guide catheter, it is beneficial to infuse the thrombolytic agent through a passage of smaller diameter such that the thrombolytic agent is directed against the occlusive material with velocity.

After the occlusive material has been treated with thrombolytic agent, the thrombectomy catheter 12 can be inserted through the guide catheter 100. As illustrated in FIG. 11, preferably the thrombectomy catheter 12 is positioned within the guide catheter 100 at a position spaced a distance "D" from a crest "C" of the sinusoidal shape. Since the crest "C" of the sinusoidal shape will be positioned adjacent a wall of the vessel 102, spacing the distal end of the thrombectomy catheter 12 a distance "D" away from the crest "C" minimizes the likelihood that the wall of the vessel 102 will be drawn into the fluid jet 50 (FIG. 5) further maximizing safety of the device. After the thrombectomy catheter 12 is properly positioned within the guide catheter 100, the thrombectomy catheter 12 can be operated in the manner discussed above to remove additional occlusive material from the vessel 102.

It is envisioned that the guide catheter 100 and thrombectomy catheter 12 can be used together without first infusing a thrombolytic agent through the guide catheter. It is further envisioned that the thrombolytic agent can be infused into the vessel 102 through the thrombectomy catheter 12, such as through the infusion lumen 32 of the catheter body 24.

Figure 13:
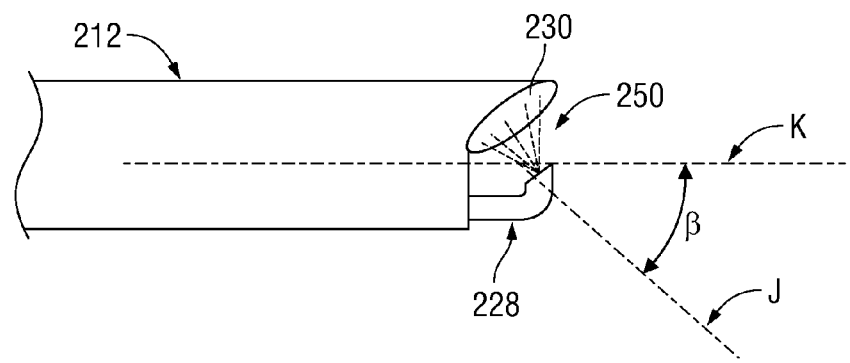
FIG. 13 is a side view of an alternate embodiment of the presently disclosed thrombectomy catheter.
Figure 14:
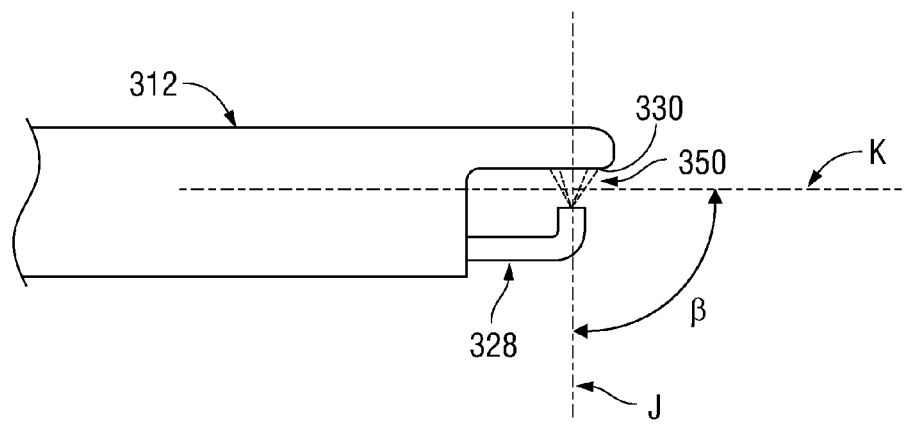
FIG. 14 is a side view of yet another embodiment of the presently disclosed thrombectomy catheter.

FIGS. 13 AND 14 illustrate alternate embodiments of the presently disclosed thrombectomy catheter shown generally as 212 (FIG. 13) and 312 (FIG. 14). Catheters 212 and 312 are substantially similar to catheter 12 except that the high pressure tube 228, 328 is configured to direct a high pressure jet 250, 350 into the exhaust lumen 230, 330 of the catheter in a direction at an angle to the longitudinal axis of the catheter. More specifically, catheter 212 includes a high pressure tube 228 which has a nozzle orifice which directs the high pressure jet 250 along an axis J which defines an angle β of between about 15 degrees and about 75 degrees with respect to the longitudinal axis K of the catheter 212. In one embodiment, β is between about 30 degrees and about 60 degrees and may be about 45 degrees. The configuration of catheter 212 facilitates easier entry of the catheter 212 into the occlusive material.

Referring to FIG. 14, the catheter 312 includes a high pressure tube 328 which includes a nozzle orifice which directs a high pressure jet 350 along an axis J which defines an angle β of about 90 degrees with respect to the longitudinal axis K of the catheter 312. Each of catheters 212 and 312 includes an infusion lumen which is not shown which is similar to the infusion lumen 32 included in catheter 12.

Figure 15:
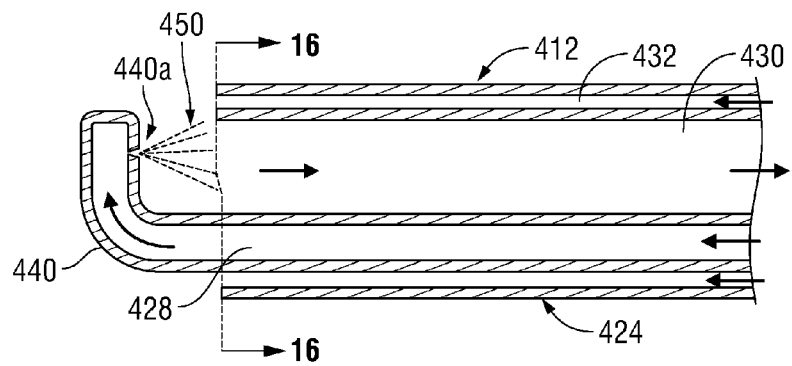
FIG. 15 is a side cross-sectional view of a distal end of another embodiment of the presently disclosed thrombectomy catheter.
Figure 16:
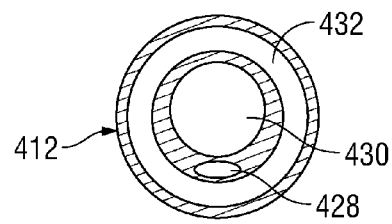
FIG. 16 is a cross-sectional view taken along section lines 16-16 of FIG. 15.

FIGS. 15 and 16 illustrate yet another alternate embodiment of the presently disclosed thrombectomy catheter shown generally as 412. Catheter 412 includes an annular infusion lumen 432, a central exhaust lumen 430 and a high pressure supply tube 428. The supply tube 428 includes a bent portion 440 defining a nozzle 440a. The nozzle 440a is positioned to direct a jet 450 of fluid into a distal end of the exhaust lumen 430. As illustrated, the catheter 412 may be integrally formed with the high pressure tube 428. Although not shown, a more rigid bent portion 440 may be provided at the distal end of high pressure tube 428 to prevent deflection of the bent portion 440 caused by ejection of the jet 450.

Figure 17:
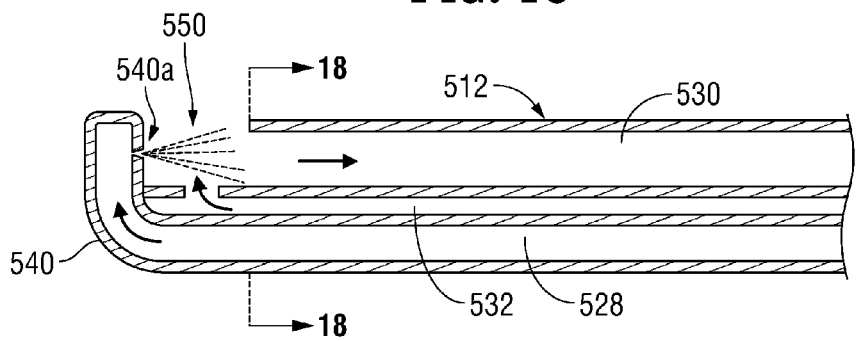
FIG. 17 is a side cross-sectional view of a distal end of another embodiment of the presently disclosed thrombectomy catheter.
Figure 18:
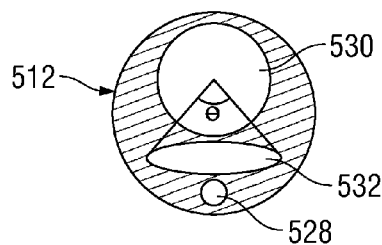
FIG. 18 is a cross-sectional view taken along section lines 18-18 of FIG. 17.

FIGS. 17 and 18 illustrate yet another embodiment of the thrombectomy catheter shown generally as 512. Catheter 512 includes a catheter body 524 defining an exhaust lumen 530, an infusion lumen 532, and a high pressure fluid supply lumen 528. A distal end of the high pressure fluid supply lumen 528 includes a bent portion 540 having a nozzle orifice 540a. The nozzle orifice 540a is positioned to direct a jet 550 of fluid into the distal end of the exhaust lumen 530. As illustrated, the infusion lumen 532 is centrally disposed in the catheter body 524 in contrast to infusion lumen 432 of catheter 412 which is positioned annularly about the catheter body 424.

Other than the different orientations and configurations of the various lumens, the embodiments shown in FIGS. 15-18 would be constructed and operate similar to the previous embodiments shown in FIGS. 1-8. The variations in the infusion lumens 432, 532, provide the ability to vary the angular coverage of the infusion lumens around the exhaust lumens anywhere between 0 and 360°. Further, the infusion lumen 532 shown in FIGS. 17-18 provide infusion directly adjacent the cutting jet 550. Maximizing the angular coverage ensures a means for maximizing recirculation of infusion fluid, which in turn minimizes the amount of blood aspirated from the body lumen.

Figure 19:
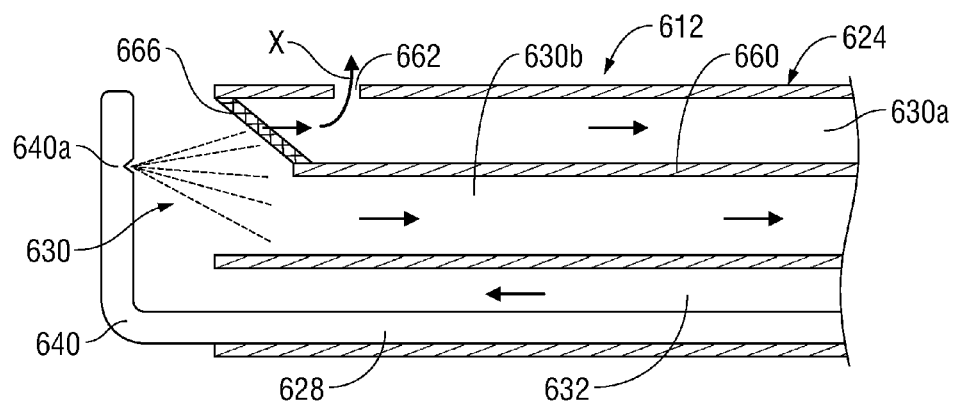
FIG. 19 is a side cross-sectional view of another embodiment of the presently disclosed thrombectomy catheter.

FIG. 19 illustrates an alternate embodiment of the presently disclosed thrombectomy catheter shown generally as 612. Catheter 612 is similar to catheter 12 and includes a catheter body 624 defining an exhaust lumen 630, an infusion lumen 632 and a high pressure fluid supply lumen 628. A distal end of the high pressure fluid supply lumen 628 includes a bent portion 640 having a nozzle orifice 640a. The nozzle orifice 640a is positioned to direct high pressure fluid into the exhaust lumen 630.

The exhaust lumen 630 includes a dividing wall 660 that divides the exhaust lumen 630 into first and second exhaust lumen sections 630a and 630b. First exhaust lumen section 630a includes a channel 662 which enables a portion of the fluid aspirated into the first exhaust lumen section 630a to be recirculated into a body lumen in the direction indicated by arrows "X". A filter 666 is provided at the inlet to the first exhaust lumen section 630a to prevent passage of solid particles, such as occlusive material and solid blood components, into the first exhaust lumen section 630a. In one embodiment, the filter 666 is positioned at angle to direct the solid particles filtered from fluid entering the first exhaust lumen section 630a into the second exhaust lumen section 630b. The proximal end of each of the exhaust lumen sections 630a and 630b communicate with an exhaust reservoir, such as reservoir 18, as discussed above with respect to system 10 shown in FIG. 1.

Figure 20:
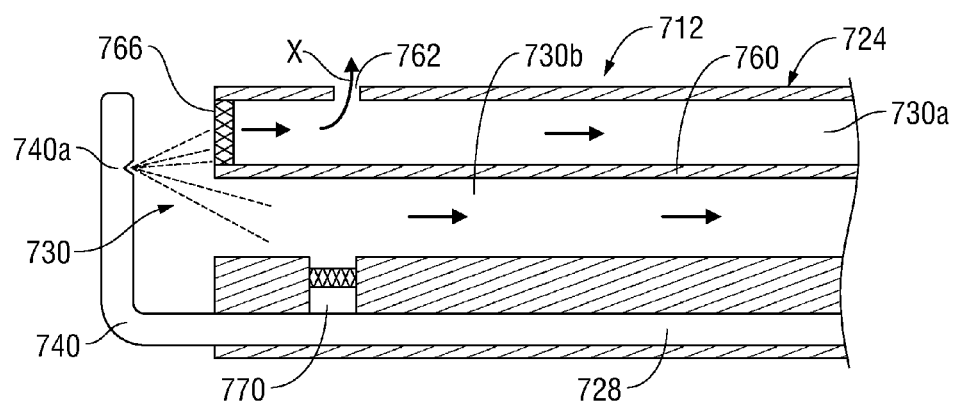
FIG. 20 is a side cross-sectional view of yet another embodiment of the presently disclosed thrombectomy catheter.

In another embodiment of the presently disclosed thrombectomy catheter, shown generally as 712 in FIG. 20, a second recirculation channel 770 is provided, as will be discussed in further detail below. Catheter 712 includes a body 724 defining an exhaust lumen 730, an infusion lumen (not shown) and a high pressure fluid supply lumen 728 which includes a bent portion 740 having a nozzle orifice 740a. The exhaust lumen 730 includes a dividing wall 760 which divides the exhaust lumen 730 into first and second exhaust lumen sections 730a and 730b. A first filter 766 is positioned in the distal end of the first exhaust lumen section 730a. The first filter 766 is similar to the filter 666 and prevents solid particles from passing into the first exhaust lumen section 730a and passing through the recirculation channel 762. The recirculation channel 762 enables a portion of the fluid entering the first exhaust lumen section 730a to enter back into the lumen of a patient. The catheter 712 differs from the catheter 612 in that filter 766 is not angled but extends across the first exhaust lumen section 730a (although the filter 766 may be angled), and in that the second recirculation channel 770 recirculates a portion of the fluid exiting the second exhaust lumen section 730b into high pressure fluid supply lumen 728. A second filter 772 is positioned within recirculation channel 770. In one embodiment, the second filter 772 has a mesh size which permits fluids and very small solid particles, for example, less than 0.0005 inches, to pass into supply lumen 728. More specifically, the solid particles should be at least an order of magnitude less in size than the nozzle orifice diameter. By enabling small solid particles to pass into the high pressure supply lumen 728, a sand blasting-like effect can be achieved from nozzle 740a to more effectively remove occlusive material from a body lumen. Although now shown, catheter 712 may be provided with only one of recirculation channels 770 and 762. In addition, although it is disclosed to supply solid particles from the exhaust lumen 730 to the high pressure supply lumen 728, it is envisioned that solid particles may be supplied to the high pressure supply lumen 728 directly from the high pressure fluid source 16 (FIG. 1).

Figure 21:
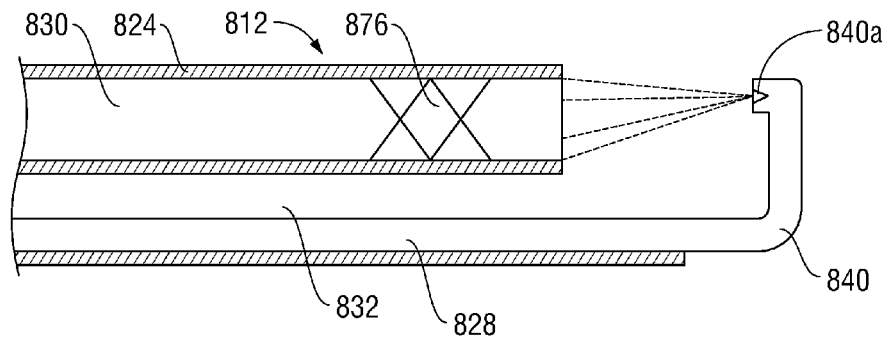
FIG. 21 is a side cross-sectional view of another embodiment of the presently disclosed thrombectomy catheter.

FIG. 21 illustrates another embodiment of the presently disclosed thrombectomy catheter, shown generally as 812. The catheter 812 includes a catheter body 824 defining an exhaust lumen 830 and an infusion lumen 832 and having a high pressure fluid supply lumen 828. The high pressure fluid supply lumen 828 includes a bent portion 840 having a nozzle orifice 840a positioned to direct high pressure fluid into the exhaust lumen 830.

The thrombectomy catheter 812 includes macerating structure 876 in the exhaust lumen 830 for breaking up the occlusive material. This may help prevent clogging of the exhaust lumen 830 by the occlusive material. The macerating structure 876 may include a component having sharp cutting edges, such as a grate or perforated plate, which is positioned to break up occlusive material which is aspirated into the exhaust lumen 830. Alternatively, the macerating structure 876 may assume a variety of configurations including a rotatable turbine or grinder which rotates in response to fluid flow through the exhaust lumen 830, or a series of abrasive projections positioned within or along the walls of exhaust lumen 830.

Figure 22:
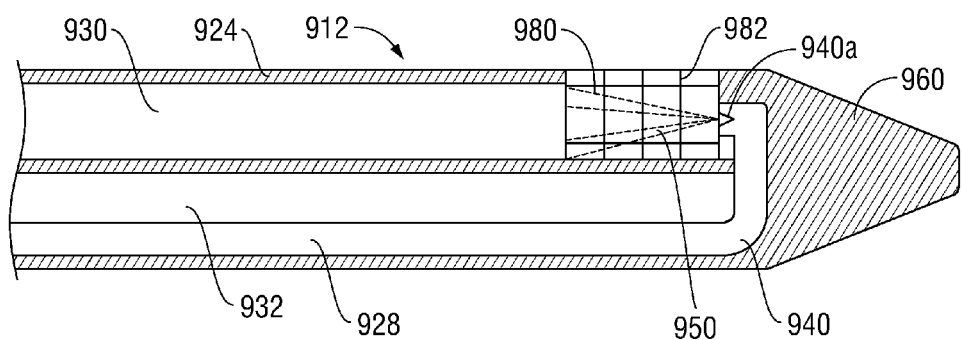
FIG. 22 is a side cross-sectional view of yet another embodiment of the presently disclosed thrombectomy catheter.

FIG. 22 illustrates yet another embodiment of the presently disclosed thrombectomy catheter shown generally as thrombectomy catheter 912. Thrombectomy catheter 912 includes a catheter body 924 defining an exhaust lumen 930 and an infusion lumen 932 and having a high pressure fluid supply lumen 928 including a bent portion 940 and a nozzle 940a. An atraumatic tip 960 is positioned about the distal end of thrombectomy catheter 912 and defines a window 980 between nozzle 940a and the inlet to exhaust lumen 930. A separator 982, such as a cage or screen structure, is positioned over the window 980. The separator 982 minimizes the amount tissue which will be drawn into the cutting window 980 to minimize the likelihood of damage to a vessel wall caused by the vessel wall coming into contact with the fluid jet 950. Although not shown, the separator 982 can be slidably positioned about or within catheter 912 such that the separator 982 can be selectively positioned over window 980 or moved away from window 980.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another exemplary embodiment without departing from the scope of the present disclosure. For example, the sensors 80a-80c which are described with respect to thrombectomy catheter 12 shown in FIG. 2 can be incorporated into any of the thrombectomy catheters described herein As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A thrombectomy catheter system comprising:
   a catheter including a catheter body and a high pressure tube, the catheter body defining an exhaust lumen and an infusion lumen, the high pressure tube defining a high pressure fluid supply lumen separate from the infusion lumen, and the high pressure tube having a nozzle orifice positioned to direct a fluid jet into a distal opening of the exhaust lumen;
   a source of infusion fluid communicating with a proximal end of the infusion lumen; and
   a fluid control device fluidly coupled between the catheter and the source of infusion fluid, the fluid control device being adapted to regulate a flow rate of infusion fluid from the source of infusion fluid to the infusion lumen of the catheter, wherein the infusion lumen delivers the infusion fluid through an infusion opening different from the nozzle orifice of the high pressure tube and different from the distal opening of the exhaust lumen, and wherein the high pressure tube extends through the infusion lumen of the catheter body.

2. The thrombectomy catheter system according to claim 1, wherein a distal portion of the high pressure tube defines a bent portion, the nozzle orifice being positioned in the bent portion.

3. The thrombectomy catheter system according to claim 2, wherein the bent portion extends along an axis which is substantially transverse to a longitudinal axis of the catheter.

4. The thrombectomy catheter system according to claim 1, further including a source of high pressure fluid communicating with the high pressure tube.

5. The thrombectomy catheter system according to claim 1, wherein the exhaust lumen is a first exhaust lumen and the infusion lumen is a first infusion lumen, further including a positioning band secured to a distal end of the catheter body, the positioning band defining a second exhaust lumen which communicates with the first exhaust lumen of the catheter body and a second infusion lumen which communicates with the first infusion lumen of the catheter body.

6. The thrombectomy catheter system according to claim 5, wherein the high pressure tube is bonded to the positioning band.

7. The thrombectomy catheter system according to claim 5, wherein the high pressure tube extends through the first infusion lumen of the catheter body and the second infusion lumen.

8. The thrombectomy catheter system according to claim 7, wherein the second infusion lumen defines a pair of concavities dimensioned to receive the high pressure tube and prevent lateral movement of the high pressure tube in relation to the positioning band.

9. The thrombectomy catheter system according to claim 1, wherein the fluid control device includes an adjustable valve configured to regulate the flow rate of infusion fluid into the infusion lumen of the catheter body from the source of infusion fluid.

10. The thrombectomy catheter system according to claim 9, wherein the adjustable valve is adapted to vary the flow rate of infusion fluid to the infusion lumen of the catheter body cyclically.

11. The thrombectomy catheter system according to claim 1, wherein the fluid control device includes a fluid pump configured and arranged to supply infusion fluid to the infusion lumen of the catheter body from the source of infusion fluid.

12. The thrombectomy catheter system according to claim 11, wherein the fluid pump is adapted to vary the flow rate of infusion fluid to the infusion lumen of the catheter body cyclically.

13. The thrombectomy catheter system according to claim 1, wherein the catheter further includes an atraumatic tip secured to the catheter body.

14. The thrombectomy catheter system according to claim 13, wherein the infusion lumen is a first infusion lumen, and wherein the atraumatic tip includes a pair of infusion channels and a central cavity, the infusion channels being in communication with a second infusion lumen of the positioning band, and the central cavity configured for receiving a distal portion of the high pressure tube, and the central cavity having an upper opening.

15. The thrombectomy catheter system according to claim 14, wherein the infusion channels extend distally of the distal portion of the high pressure tube.

16. The thrombectomy catheter system according to claim 1, further including a guide catheter defining a guide lumen dimensioned to receive the thrombectomy catheter, a proximal balloon, and a distal balloon.

17. The thrombectomy catheter system according to claim 16, wherein a portion of the guide catheter between the proximal balloon and the distal balloon has a sinusoidal shape and defines a plurality of openings which provide access to the thrombectomy catheter.

18. The thrombectomy catheter system according to claim 16, wherein a portion of the guide catheter between the proximal balloon and the distal balloon is flexible and defines a plurality of openings which provide access to the catheter, the flexibility of the portion of the guide catheter is such that a sinusoidal shape imparted to thrombectomy catheter is taken by the guide catheter once the thrombectomy catheter is inserted into the guide catheter.

19. The thrombectomy catheter system according to claim 1, further including a sensor configured to measure the pressure within a body lumen.

20. The thrombectomy catheter system according to claim 19, wherein the sensor is configured to control operation of the fluid control device configured to be fluidly connected to the infusion lumen and operable to control a flow rate of the infusion fluid through the infusion lumen.

21. The thrombectomy catheter system according to claim 1, further including a macerating structure positioned within the exhaust lumen and configured to break up occlusive material.

22. The thrombectomy catheter system according to claim 21, wherein the macerating structure includes a grate having sharp cutting edges.

23. The thrombectomy catheter system according to claim 21, wherein the macerating structure includes a rotatable turbine configured to grind occlusive material.

24. The thrombectomy catheter according to claim 1, further including a body defining a cutting window between the nozzle orifice and an inlet to the exhaust lumen, and a separator positioned adjacent the window to cover the window, wherein the separator is configured to minimize the amount of tissue entering the cutting window.

* * * * *